(12) United States Patent
Ude

(10) Patent No.: US 10,281,394 B2
(45) Date of Patent: May 7, 2019

(54) APPARATUS, METHOD AND SYSTEM FOR RECORDING AT LEAST ONE VARIABLE DURING A BIOLOGICAL/CHEMICAL PROCESS

(71) Applicant: PreSens Precision Sensing GmbH, Regensburg (DE)

(72) Inventor: Christian Matthias Ude, Laatzen (DE)

(73) Assignee: PreSens Precision Sensing GmbH, Regensburg (DE)

( * ) Notice: Subject to any disclaimer, the term of this patent is extended or adjusted under 35 U.S.C. 154(b) by 0 days.

(21) Appl. No.: 15/936,991

(22) Filed: Mar. 27, 2018

(65) Prior Publication Data
US 2018/0284019 A1 Oct. 4, 2018

(30) Foreign Application Priority Data

Mar. 31, 2017 (DE) .................. 10 2017 107 033

(51) Int. Cl.
*G01N 21/00* (2006.01)
*G01N 21/51* (2006.01)
(Continued)

(52) U.S. Cl.
CPC .......... *G01N 21/51* (2013.01); *B01F 11/0014* (2013.01); *C12M 27/16* (2013.01);
(Continued)

(58) Field of Classification Search
CPC ........ G01N 21/29; G01N 33/32; G01N 21/05; G01N 21/293; G01N 33/2888
(Continued)

(56) References Cited

U.S. PATENT DOCUMENTS 6,673,532 B2    1/2004  Rao
7,339,671 B2    3/2008  Peng
(Continued)

FOREIGN PATENT DOCUMENTS

DE    102011000891    8/2012
DE    102014001284    1/2015
(Continued)

OTHER PUBLICATIONS www.sigmaaldrich.com, Microtiter plates, publication date unknown, last accessed Jun. 14, 2018.

*Primary Examiner* — Md M Rahman
(74) *Attorney, Agent, or Firm* — Simpson & Simpson, PLLC

(57) ABSTRACT

An apparatus, a method and a system for the parallelized recording of at least one variable during a biological/chemical process are disclosed. A matrix, which has at least one container and which can be positioned on a measurement carrier, is provided to accommodate the liquid samples. A measuring unit, which comprises a controllable radiation source for electromagnetic radiation and at least one sensor for detecting electromagnetic radiation, is fixedly disposed in or on the measurement carrier. When at least one matrix with the containers is placed onto the measurement carrier, the respective measuring unit is assigned to the base of each container from the outside. During the measurement by the measuring unit, a movement device is used to move the measurement carrier with a defined radial movement about a fixed axis orthogonal to the gravitational force.

6 Claims, 9 Drawing Sheets

(51) Int. Cl.
  *B01F 11/00* (2006.01)
  *C12M 1/34* (2006.01)
  *G01N 21/25* (2006.01)
  *C12M 3/06* (2006.01)
  *G01N 33/52* (2006.01)
  *G01N 21/27* (2006.01)
  *G01N 21/80* (2006.01)
  *G01N 21/17* (2006.01)
  *G01N 21/77* (2006.01)

(52) U.S. Cl.
  CPC ............ *C12M 41/26* (2013.01); *C12M 41/32* (2013.01); *C12M 41/36* (2013.01); *G01N 21/253* (2013.01); *G01N 21/272* (2013.01); *G01N 33/52* (2013.01); *G01N 21/80* (2013.01); *G01N 2021/1789* (2013.01); *G01N 2021/7786* (2013.01)

(58) Field of Classification Search
  USPC ........................................................ 356/441
  See application file for complete search history.

(56) References Cited

U.S. PATENT DOCUMENTS

| | | |
|---|---|---|
| 8,405,033 B2 | 3/2013 | Debreczeny |
| 8,603,772 B2 | 12/2013 | Debreczeny et al. |
| 2005/0176155 A1 | 8/2005 | Klein et al. |
| 2016/0282106 A1* | 9/2016 | Falkenstein ............ G01B 11/02 |
| 2018/0011027 A1 | 1/2018 | Herzog et al. |

FOREIGN PATENT DOCUMENTS

| | | |
|---|---|---|
| EP | 1730494 | 12/2006 |
| WO | WO2016066156 | 5/2016 |

* cited by examiner

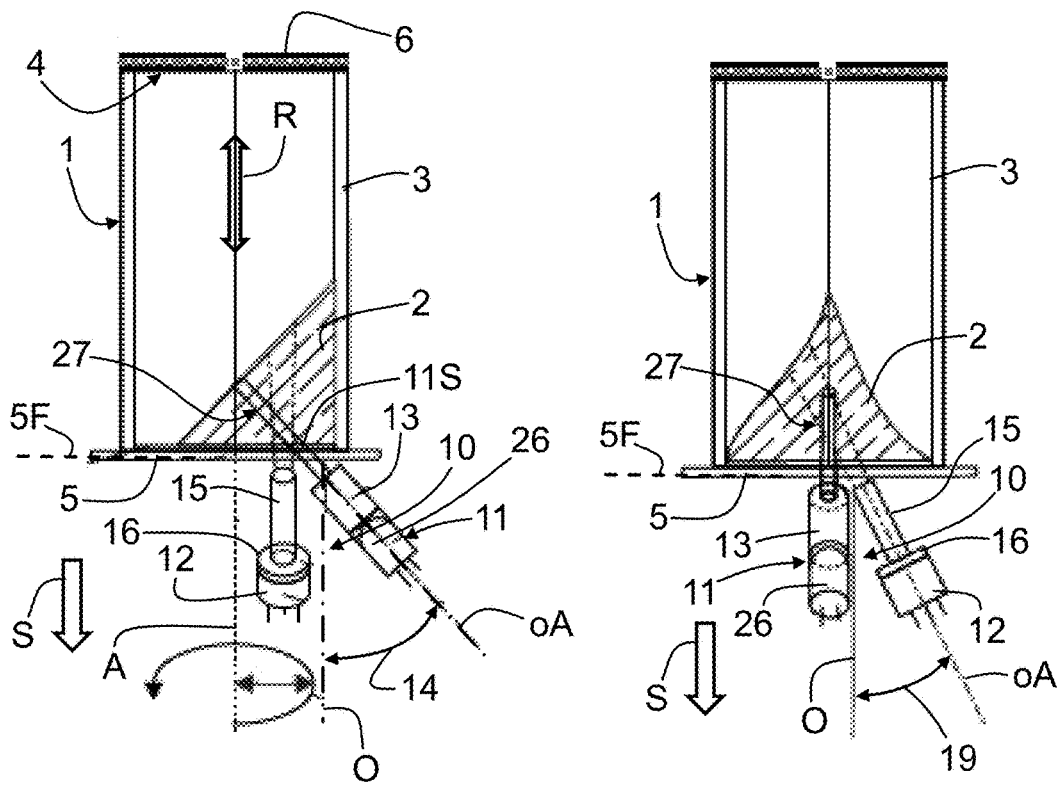
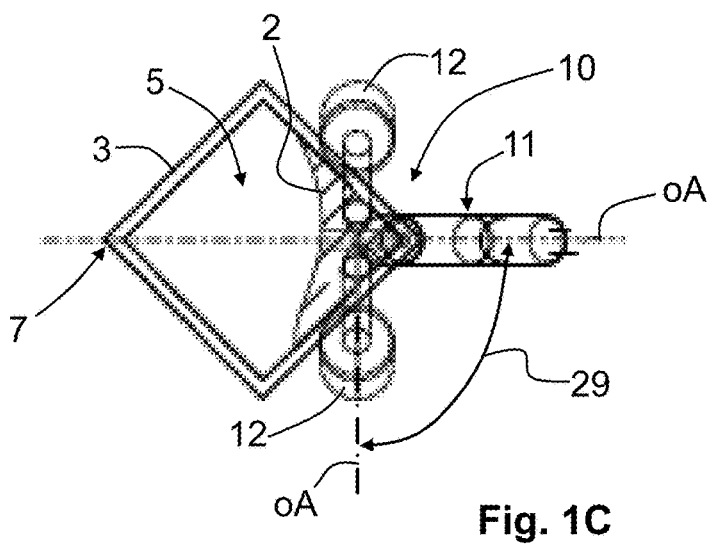

APPARATUS, METHOD AND SYSTEM FOR RECORDING AT LEAST ONE VARIABLE DURING A BIOLOGICAL/CHEMICAL PROCESS

CROSS-REFERENCE TO RELATED APPLICATIONS

This patent application claims the benefit under 35 U.S.C. § 119 of German Patent Application No. 10 2017 107 033.8, filed Mar. 31, 2017, which application is incorporated herein by reference.

FIELD OF THE INVENTION

The invention relates to an apparatus for recording at least one variable in a plurality of containers for liquid samples during a biological/chemical process.

The invention further relates to a method for recording at least one variable in a plurality of containers for liquid samples during a biological/chemical process in a liquid sample.

The invention also relates to a system for recording at least one variable in a plurality of containers for liquid samples during a biological/chemical process involving liquid samples.

BACKGROUND OF THE INVENTION

The European Patent Specification EP 1 730 494 B1 discloses a method and an apparatus for recording process parameters of reaction liquids in a plurality of microreactors that are shaken continuously, at least until the end of the reaction in all of the microreactors. The process parameters in the microreactors are recorded during the reaction with the aid of at least one optical sensor system. The optical sensor system is not moved during the recording of the values of a process parameter, for example during the recording of a current value of the autofluorescence of the reaction liquid. The thereby occurring relative movement between the shaken microreactors and each optical sensor system is unproblematic if, during the recording of the process parameters in one of the microreactors, the electromagnetic radiation from each optical sensor system is introduced exclusively into this microreactor and the radiation emanating from the reaction liquid strikes only on the sensor of the associated optical sensor system. The measurement is carried out in continuously shaken reactors, wherein each optical sensor system aligned under the microreactors of the microtiter plate is not moved, at least during the recording of the process parameters, so that the shaken microreactors can move relative to each optical sensor system.

U.S. Pat. No. 8,405,033 B1 discloses a sensor for the rapid determination of a particle concentration in a liquid. The particle concentration is measured through the wall of a container. Different types of containers can be used. The sensor comprises one or more light sources and one or more sensors accommodated in a sensor housing. According to one possible embodiment, the container can also be a well plate. A light source and a sensor are associated with the base of each well.

U.S. Pat. No. 8,603,772 B2 discloses a method and an apparatus for determining particle size and/or particle concentration. For this purpose, one or more light sources and one or more detectors are accommodated in a housing that is in contact with a medium to be examined. The apparatus is also suited for the non-invasive measurement of biomass in a bioreactor.

U.S. Pat. No. 6,673,532 B2 discloses a bioreactor that uses a non-invasive optical-chemical detection method. A light source excites an optical-chemical sensor, the optical reaction of which is measured by a detector. According to one embodiment, each reactor is associated with an LED and a detector. In this case, illumination occurs through a side wall of the container. Detection takes place through another side wall of the container.

U.S. Pat. No. 7,339,671 B2 discloses a method and an apparatus for real-time and online monitoring of the cell growth and the concentration in a dynamic cell culture environment. Techniques that suppress noise from ambient light, non-uniform scattering distribution and reflection effects in a dynamic environment are used.

German Patent DE 10 2014 001 284 B3 discloses an apparatus and a method for determining the optical density and/or the change in the optical density of a reaction mixture in a shaken reactor. In this case, light passes from at least one light source into the reaction mixture. The light leaving the reaction mixture is detected by at least one light sensor. During the detection of the light by at least one light sensor, the reactor and the reaction mixture are shaken. The detection of the light by at least one light sensor takes place at a frequency at which the shaking frequency is not a whole number multiple of the detection frequency, so that at least two measurement points detected in a specific time interval by at least one light sensor are combined to one measurement series. The reaction mixture is shaken continuously. There is no relative movement between the reactor, the light sources and the light sensors during the recording of a measurement series.

The International Patent Application WO 2016/066156 relates to a mobile photometric measuring apparatus comprising with at least one measuring module, which comprises a light source, a detector and an optical structure having an optical system with integrated filter properties. An optical system and at least one filter can likewise be provided. Said components are arranged on a circuit board in a housing and/or connected to a component. The invention further relates to a mobile photometric measuring method on microtiter plates with grid sensors.

The German Patent Application DE 10 2011 000 891 A1 discloses a method and an apparatus for determining at least one variable of a sample located in a moving container. The container is moved in a defined manner and at least one variable is determined. The determination of at least one variable is coordinated with a state of movement of the sample which results from the movement of the container. To implement the method, a carrier element is provided for the container with which a defined movement can be executed. A measuring system is provided as well, by means of which at least one variable of the sample can be determined. At least one means for synchronization is provided, by means of which the determination of at least one variable can be temporally coordinated with a state of movement of the sample that can be generated by the movement of the container.

Microtiter plates, which represent a matrix of a plurality of containers rigidly connected to one another, are well known from the prior art (see www.sigma-aldrich.com).

In numerous studies in various fields, for example chemistry, pharmacy or life sciences, samples are analyzed in containers that are moved to support the processes of interest in the respective study. This is preferably done mechanically; the appropriate devices, for example agitators, shakers or rockers, are familiar to the person skilled in the art. These devices are commercially available in embodiments that can move one container, or even a plurality of containers simultaneously, in a defined manner. The purpose of the movement is usually a mixing of the sample, which is present in the form of a fluid medium or liquid, for example a solution, emulsion or suspension; the sample can also be a fluid medium in which microorganisms are developing.

BRIEF SUMMARY OF THE INVENTION

The object of the invention is therefore to create an apparatus for recording at least one variable in a plurality of containers for liquid samples during a biological/chemical process, which allows interruption-free, non-invasive and simultaneous measurement on a plurality of containers over extended periods of time under reproducible conditions.

The object of the invention is also to create a method for the parallelized recording of at least one variable in a plurality of containers for liquid samples during a biological/chemical process, which allows interruption-free, non-invasive and simultaneous measurement on a plurality of containers with a liquid sample over extended periods of time under reproducible conditions.

This object is achieved by means of a method for recording at least one variable in a plurality of containers for liquid samples during a biological/chemical process that comprises the features of Claim 8.

The object of the invention is further to create a system for recording at least one variable in a plurality of containers for liquid samples during a biological/chemical process, which allows interruption-free, non-invasive and simultaneous measurement on a plurality of containers over extended periods of time under reproducible conditions.

This object is achieved by means of a system for recording at least one variable in a plurality of containers for liquid samples during a biological/chemical process that comprises the features of Claim 14.

The apparatus according to the invention is used for the parallelized recording of at least one variable in a plurality of containers for liquid samples during a biological/chemical process. Said variables are typically the turbidity and the optical density of liquid samples, as well as in particular the cell density, biomass and cell concentration, pH value, $O_2$ saturation of the liquid and the ambient temperature.

For this purpose, the apparatus according to the invention has a measurement carrier in or on which a plurality of measuring units are fixedly disposed. Each measuring unit comprises at least one controllable radiation source for electromagnetic radiation and at least one sensor for detecting electromagnetic radiation. The measurement carrier can be designed to be movable in the x-coordinate direction and in the y-coordinate direction in such a way that the measurement carrier executes a composite movement in the X/Y plane. The containers are arranged in the form of a matrix. The matrix comprises the plurality of containers, each of which has a square cross-sectional shape. Each of the containers is defined by a peripheral wall and a base. The base closes the respective container. As is known of a matrix, the plurality of containers are arranged in columns and rows and are therefore all rigidly connected to one another. Microtiter plates are designed in such a way that they enclose the containers having the square cross-sectional shape, which are configured to accommodate one respective liquid sample. For the measurement, the matrix is connected to the measurement carrier in a detachable but fixed manner.

The containers are arranged in the matrix in such a way that each container comprises four individual walls, which are arranged in pairs at an angle of 90°. When the matrix is detachably connected to the measurement carrier, a measuring unit is assigned to each container of the matrix at its base in order to record the measurement data. Each measuring unit can include a controllable radiation source for electromagnetic radiation and at least one sensor for detecting electromagnetic radiation from the container. According to the preferred embodiment of the invention, a measurement region for the measuring unit associated with the respective container is formed in the region of a corner and at the base of each container. In the area of the corner of the measurement region, a liquid column sufficiently large for the measurement by the measuring unit is formed as a result of the shaking movement. The entire base of each container, or at least a section thereof, can be transparent to the electromagnetic radiation entering the container and exiting from the container.

The electromagnetic radiation detected by at least one sensor is scattered electromagnetic radiation that is continuously recorded by the sensor. In this process, the scattered light can be produced by physical processes, such as reflection at interfaces and diffraction, as a function of the refractive index of the material present in the sample. The scattered electromagnetic radiation thus also occurs as a result of the scattering at the biological material present in the respective container. According to one possible embodiment, the electromagnetic radiation can be light with a wavelength of 600-900 nm.

With the apparatus according to the invention, changing process parameters of cell suspensions in continuously and non-continuously shaken containers can be recorded in an automated and temporally parallel manner. In order to produce a movement of the measurement carriers for the containers, a movement composed of an x-coordinate direction and a y-coordinate direction can be provided. The measurement carrier can thus be movable with a defined radial movement about a fixed axis, orthogonal to the gravitational force.

The advantage of the apparatus according to the invention is that changes in turbidity, and changing cell and biomass concentrations in the containers resulting from cell proliferation processes of living cultures, can be monitored and recorded over the entire cultivation time. In doing so, different samples in different incubation environments, and the reaction of said samples to reagents, can be examined in a temporally parallel manner. In addition, for a measurement of the cell and biomass concentrations, the containers do not have to be transported to a measuring apparatus, for example at another location. According to the invention, the measurement can be carried out in an automated manner and at any points in time without the need for operating personnel.

Every container of the matrix is open on the side opposite to the base. Each container of the matrix can be filled individually with the corresponding sample through said opening. After filling, the matrix of containers is provided with a cover. The electromagnetic radiation source is disposed in the measuring unit in such a way that a beam emanating from the radiation source is arranged at an angle between 30° and 45° to the orthogonal to the bottom surface of each container. The angle is preferably between 36°-42°; particularly preferably 39°.

The sensor is disposed in the measuring unit in such a way that, for each container of the measurement carrier, an optical fiber of the sensor or an optical axis of the sensor is disposed in such a way that the optical fiber or the optical axis is arranged at a 25° to 30° angle to an orthogonal to the bottom surface of the respective container. Particularly preferably, the angle is 27°.

The radiation source preferably comprises at least one light-emitting diode, to which an optical system for steering and shaping (collimating) the electromagnetic radiation with a wavelength of 600-900 nm is arranged downstream. The light of the light-emitting diode is radiated through the optical system into the respective associated container. Essentially whereby the lens (74) collimates the electromagnetic radiation in the liquid sample to the shape of a cylinder (27).

According to one possible embodiment, at least one sensor is coupled with an optical fiber and at least one optical filter. The radiation source and the optical fiber of the sensor are arranged at an angle to one another in the measuring unit. The radiation source and the optical fiber are preferably arranged at a defined angle of 90° to one another.

Each measurement carrier is preferably provided with an electronics module, by means of which there is also a data connection (e.g. a radio link) to a base station. The electronics module is also used to supply power to the light-emitting diode, and if necessary to the sensors, for controlling the light-emitting diode of each measuring unit of each container and for the recording of the measured values by the sensor of the measuring unit.

By means of a cylindrical light-emitting diode with a diameter of at most 3 mm and radiant power of at least 7000 mCd, and in combination with the downstream optical system (collimator), electromagnetic radiation with a dominant wavelength in the range of 600-900 nm is radiated into the respective container (microbioreactor of the matrix) through the base, which is permeable to the radiation, or at least through the permeable measurement region. The beam is collimated to form a light cylinder in the liquid sample, which has a diameter of at most 1.5 mm and a length of at least 10 mm from the exit location. The scattered light produced on the sample is guided through an optical filter to the sensor of the measuring unit via at least one optical fiber. Low-noise Si photodiodes, for example, with an integrated amplifier and a measuring frequency of at least 10 kHz that are suitable for coupling to optical fibers can be used as the sensors or light sensors.

One possible design of the matrix of containers can be that each of the containers is a square microbioreactor with a transparent base, which is located above the sensor of the measuring unit of the measurement carrier for recording turbidity, biomass concentration and cell concentration. A plurality of the square microbioreactors are arranged in the matrix, and the matrix is moved continuously about a fixed axis with a radius of 1-30 mm and a frequency of 0-600 rpm. The sample is thus centrifuged toward the walls (side walls) of the microbioreactor, and a liquid column is formed in the corners so that ample measurement signals can be produced in the measurement region.

The method according to the invention is used for determining at least one variable in a plurality of containers for liquid samples of a biological/chemical process in a liquid sample in at least one moving or non-moving container of a matrix. The essential aspects of the method according to the invention are the movement of the plurality of containers, which are arranged in the form of a matrix and are rigidly connected to one another, in a defined manner, and the determination of at least one variable of the liquid sample, wherein the determination is temporally coordinated with a signal pattern of the individual liquid samples resulting from the movement of the container. Prior to the actual measurement, at least one of the plurality of containers arranged in the form of a matrix is filled, wherein the matrix is arranged on the measurement carrier fixedly and in a defined manner. When the measurement carrier is moved, at least one variable can be determined during the biological/chemical process. The movement of the measurement carrier is executed without interruption and with a defined, radial movement (composed of an x-coordinate direction and a y-coordinate direction) about a fixed axis, orthogonal to the gravitational force. In each container in which there is a sample, the variable of the sample is determined with the measuring unit of the measurement carrier permanently assigned to the container. The measuring units are arranged in the measurement carrier in such a way that, when the matrix is positioned on the measurement carrier, one measuring unit is assigned to each container. The measuring unit comprises a controllable radiation source and at least one sensor, with which at least one variable of the sample in the respective container is recorded in a localized manner.

To record at least one variable of the sample, electromagnetic radiation is radiated by the radiation source through the base of the respective container into the sample. The scattered electromagnetic radiation of at least one variable of the sample is then received through the base by at least one sensor of the measuring unit. A continuous, optical measurement and recording of scattered light, produced on the biological material as a result of the irradiation with electromagnetic radiation, can be carried out by means of the sensor. At least one variable can be determined with the aid of the electromagnetic radiation scattered by suspended particles or by biological material. This optical response is recorded by the sensor permanently assigned to the respective container.

The variable can be the pH. Another variable can be the relative saturation of dissolved oxygen in the sample, which can likewise be recorded as an optical response by the sensor associated with the respective container. The relative saturation of dissolved oxygen in the respective liquid sample can be regulated by changing the energy input during the movement of the containers or the carrier.

Chemosensors attached to the base of the microbioreactors are used to measure the pH and the concentration of dissolved oxygen in the containers (microbioreactors). The chemosensors contain photoluminescent dyes, which emit electromagnetic radiation with a specific wavelength in a defined manner when irradiated with electromagnetic radiation of a specific wavelength. Upon direct contact with the sample in the microbioreactors, the chemosensors react with a change in the intensity and decay time of the luminescence, which, after measurement by a light sensor, can be converted into the parameters, such as pH and concentration of the dissolved oxygen, using mathematical methods.

The radiation source preferably comprises at least one light-emitting diode that is associated with an optical system for directing the electromagnetic radiation. The electromagnetic radiation is light with a wavelength of 600-900 nm. At least one variable can be recorded independently of the geometric dimension of a radial deflection by the movement. The measuring method records the measured values via the sensor with a high measuring frequency, which allows 5,000 to 100,000 individual measured values to be generated as the height of the liquid column above the stationary sensor fluctuates periodically.

A high measuring frequency of the light sensor is essential for high-resolution recording of the periodically changing level of the scattered light signal. In order to extract measurement data for correlation with reference values ($OD_{600}$, bio dry mass, cell concentration) using periodically recurring constant areas within the measurement signal, said frequency can be in the higher kHz or MHz range.

For a conversion into reference values such as optical density, biomass or cell concentration, at a fixed point in time (generally after the start of the process or the reaction) and using suitable mathematical methods, the scattered light signal measured by the sensor of the measuring unit is calculated from a defined interval of the raw data. The calculation is performed in a base station (such as a computer), to which each measurement carrier is connected via a data connection. The communication between the carrier and the base station is preferably wireless.

The mathematical analysis method runs on the base station, wherein the obtained time-resolved scattered light signal profile with at least 10,000 measurement events/second is converted into a single measured value recorded at a fixed point in time after the start of the process. The mathematical analysis method is designed in such a way that measurement data of periodically recurring areas within defined areas, which satisfy criteria defined in advance, are selected and processed further.

First and foremost, the system according to the invention makes a simultaneous monitoring of variable process parameters of highly parallelized biological and (bio)chemical processes possible. This can be done with up to 240 containers (such as microbioreactors) with a working volume of 500-11000 µl, for example, within one incubation/shaking environment. The extreme miniaturization of the measurement carriers for respective at least microtiter plates (matrix of 24 containers) makes the use of at least one measurement carrier per incubation environment and/or shaker environment possible. A number of consolidated measurement carriers can be used in different incubation and/or shaking environments, thus allowing technical test parameters such as temperature, $O_2/CO_2$ saturation of the ambient air and the shaking frequency to be changed.

The system according to the invention for the parallelized recording of at least one variable in a plurality of containers for liquid samples during a biological/chemical process, comprises a plurality of containers (microbioreactors with a square cross section) to accommodate a liquid sample. The containers are consolidated to form a matrix. The containers are thus fixedly positioned by the matrix on at least one measurement carrier in a number of columns and rows. The measurement carrier itself has a plurality of measuring units. One measuring unit is respectively assigned to the base of each container of the matrix, which is fixedly positioned on and connected to the measurement carrier. The measuring unit comprises a controllable radiation source for electromagnetic radiation and at least one sensor for detecting the electromagnetic radiation. Each measurement carrier has an electronics module, or an electronics module, which serves to control the radiation source and detects the electromagnetic radiation via the sensor, is arranged on the measurement carrier. A movement device ensures that at least one measurement carrier can be moved with a defined radial movement about a fixed axis, orthogonal to the gravitational force.

According to a possible further development of the invention, the movement device can be accommodated in an incubator together with at least one measurement carrier.

A base station can communicate with at least one measurement carrier in the incubator via the electronics module. The communication of the base station with at least one measurement carrier in the incubator can be provided via a data connection (e.g. a radio link (Bluetooth, WLAN)). The extreme miniaturization of the measurement carriers for microtiter plates of twenty-four respective containers (microbioreactors) makes the use of at least one measurement carrier per incubation environment possible. Several measurement carriers (up to ten measurement carriers) can be accommodated on the movement device in the incubator. This advantageously results in an interruption-free, non-invasive and simultaneous measurement on a plurality of containers, also on a plurality of carriers.

The individual containers advantageously have a square cross section and a volume of 500 to 11000 µl to accommodate the liquid sample. A plurality of measurement carriers can be positioned in a plurality of different incubators, so that the measurement carriers are subjected to different incubation environments and movements of the movement device. The advantage of this is that different incubation and/or shaking environments can be implemented for the same samples. A variation of the technical test parameters, such as temperature, $O_2/CO_2$ saturation of the ambient air and shaking frequency can thus easily be put into effect.

The measurement carriers in the plurality of incubators are preferably connected wirelessly to the base station (e.g. via WLAN or Bluetooth). A further embodiment defines combinations of wirebound and wireless communications for the invention.

For a wired or a wireless transfer of data, the measuring units on a shaker platform within an incubation environment and the communication structure between the individual measuring units and a base station for data processing/data recording require an electric device. Every measuring unit has a radio transmitter/receiver, for example, via which a local radio network to a permanent, central radio transmitter/receiver is established. Bluetooth or WLAN, for example, can be used for the data transfer technology being employed. In one possible embodiment, all the measuring units or their electronic units have a device-internal permanent data memory for recording measurement data. The central radio transmitter/receiver is connected to a device for data processing/data recording, such as a computer, via a data interface. Computers include desktop computers, notebook computers, tablet computers or smart phones.

The invention makes possible an apparatus, a method and a system for the automated and parallelized recording of at least one variable process parameter of cell suspensions in continuously and non-continuously shaken, square containers (microbioreactors) defining a matrix. Continuous monitoring of critical process parameters in the field of commercial biotechnology and R&D is essential for the assessment of growth processes or the division capacity of cell cultures (prokaryotes and eukaryotes). This measurable property of cells is used to identify optimum cultivation conditions, beneficial nutrients and substrates, beneficial cell strains and genetic variants, growth inhibitors and toxins from among a large number of variations.

The advantage of the invention is that changes in turbidity, and changing cell and biomass concentrations resulting from cell proliferation processes of living cultures, can be monitored and recorded over the entire cultivation time. The underlying measurement principle is based on the radiation of electromagnetic waves into the cell suspensions present in the containers, wherein each container comprises a radiation source that is stationary relative to the container and to which is assigned a corresponding light sensor. All measurement processes can be initiated and recorded in both a continuous and a non-continuous shaking operation.

The fields of application of the invention are primarily in the simultaneous monitoring of variable process parameters of highly parallelized biological and (bio)chemical processes with up to 240 500-11,000 µl containers within an incubation/shaking environment. The extreme miniaturization of the measurement carriers for twenty-four respective containers makes the use of at least one measurement carrier per incubation environment possible.

The plurality of containers consolidated to form a matrix, referred to as a microtiter plate, is made of plastic, by means of an injection molding or molding process. The plastic can be polycarbonate or polystyrene, for example.

The recorded process parameters are typically turbidity and optical density, as well as in particular cell density, biomass and cell concentration, pH, $O_2$ saturation of the liquid and the ambient temperature.

The integration of as many measurement carriers as possible in (cell culture) incubators is achieved by means of a high degree of miniaturization of the measurement carriers and the measuring units.

Possible fields of application are, in particular, screenings (strain selection, genetic selections, toxicity tests) and bioprocess development operations (media optimization, substrate selection, optimization of the $O_2$ input) in which biological or chemical changes in the turbidity of suspensions are monitored, and reaction parameters within the same incubation environment have to be compared with one another.

BRIEF DESCRIPTION OF THE DRAWINGS

The invention and its advantages are described in more detail in the following with reference to the attached drawings.

FIG. 1A shows a schematic side view of a container having a square cross section for a sample, with the associated measuring unit.

FIG. 1B shows a schematic side view of a container for a sample with the associated measuring unit, wherein, in comparison to FIG. 1A, the view is rotated 90° about the axis.

FIG. 1C shows a plan view onto the container having a square cross section and the associated measuring unit.

Figure 2:
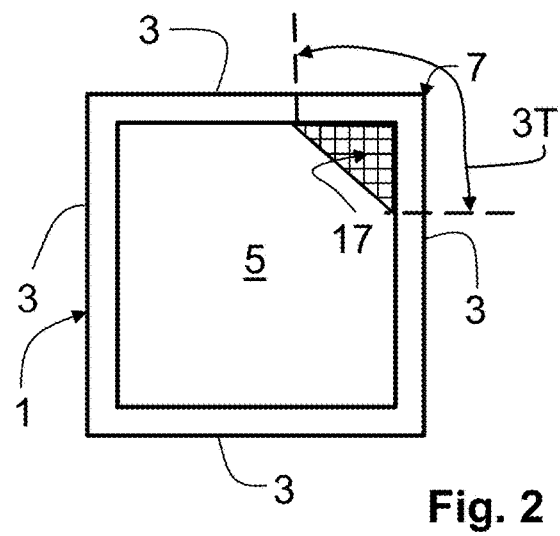
FIG. 2 shows a plan view onto the container having a square cross-sectional shape, wherein the measurement area is depicted in a corner.

The drawings merely show embodiments of how the container(s) according to the invention of the apparatus according to the invention can be configured. The drawings expressly do not represent any restriction of the invention to said embodiments.

DETAILED DESCRIPTION OF THE INVENTION

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodologies, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Moreover, as used herein, the phrases "comprises at least one of" and "comprising at least one of" in combination with a system or element is intended to mean that the system or element includes one or more of the elements listed after the phrase. For example, a device comprising at least one of: a first element; a second element; and, a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. A similar interpretation is intended when the phrase "used in at least one of:" is used herein. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Although any methods, devices or materials similar or equivalent to those described herein can be used in the practice or testing of the invention, the preferred methods, devices, and materials are now described.

FIG. 1A shows a schematic side view of the design of a container 1, as configured in a matrix 1M (see FIG. 5), for a sample 2 with a measuring unit 10 associated with the container 1. According to one possible embodiment, a plurality of said container 1 can be consolidated to form the matrix 1M, wherein the matrix 1M can be fixedly and rigidly attached to a measurement carrier 22 (see FIG. 5C or 6B). A fluid medium or a liquid, which is present in the form of a solution, an emulsion or a suspension, for example, should be considered to be the sample 2. The sample 2 can also be a fluid medium in which microorganisms are developing. The container 1 is defined by a peripheral wall 3 and a base 5. Across from the base 5, the container 1 has an opening 4, through which the sample 2 can be filled into the container 1. The opening 4 of the container 1 can, if necessary, be closed with a cover 6. The base 5 is designed in such a way that, for both directions R orthogonal to the base 5 or a bottom surface 5F, it is permeable to electromagnetic radiation (light) that is used for illumination and detection. At least one measurement on the sample 2 serves to obtain information by means of an optical method, wherein the determination of at least one variable (such as, for example, turbidity, biomass or cell concentration) takes place during an uninterrupted, defined, radial movement of the container 1 about a fixed axis A orthogonal to the gravitational force. The radius of the movement can be between 1-50 mm. The frequency of the movement can be between 0-600 revolutions per minute (rpm).

For illumination and detection, one measuring unit 10 is assigned to each base 5 outside of each container 1 of the matrix 1M. The measuring unit 10 comprises at least one controllable radiation source 11 and at least one sensor 12 for determining at least one variable of the sample 2 in the container 1. The radiation source 11 comprises a light-emitting diode 26, for example, to which an optical system 13 for steering, shaping and transmitting electromagnetic radiation with a defined wavelength is assigned. The beam 11S is collimated by the optical system 13 in such a way that a light cylinder 27 is produced in the sample 2.

According to one possible embodiment, the wavelength is 600-900 nm. The beam 11S of the radiation source 11 is directed into the respective associated container 1 at a defined angle 14. The defined angle 14 between the beam 11S or the optical axis oA of the radiation source 11 and the orthogonal O to the base 5 is between 30°-45°. The defined angle 14 is preferably between 36°-42°. The sensor 12 is coupled to an optical fiber 15 and at least one optical filter 16.

As schematically shown in FIG. 1B, the sensor 12 is arranged at a defined angle 19 with respect to the base 5 of the container 1. The angle 19 between the orthogonal O to the base 5 and the optical fiber 15 of the sensor 12, or the optical axis oA thereof, is set between 25°-30°. The angle 19 is preferably 29°.

The container 1, and therefore the entire matrix 1M, is moved in a defined manner. The determination of at least one variable of a sample 2 in a container 1 takes place during an uninterrupted, defined, radial movement of the container 1, i.e. the matrix 1M, about a fixed axis A orthogonal to the gravitational force S.

FIG. 1B shows a schematic side view of a container 1 for a sample 2 with the associated measuring unit 10, wherein, in comparison to FIG. 1A, the view is rotated 90° about the axis A.

As an example, FIG. 1C shows a plan view onto a container 1 of the matrix 1 with the associated measuring unit 10. The container 1 has a square cross section. The square cross-sectional shape described here should not be construed as a limitation of the invention. The measuring unit 10 is associated with the container 1 under the base 5 of the container 1. The measuring unit 10 is disposed in or on a measurement carrier 22 not depicted here. The matrix 1M with the containers 1 is placed onto the measurement carrier 22 in such a way that at least one radiation source 11 and at least one sensor 12 of the measuring unit 10 are assigned to each base 5 of the containers 1 of the matrix 1M.

As shown in FIG. 1C, the shaking movement of the matrix of containers 1 always results in an accumulation of the liquid sample 2 in one corner 7 (meeting of two walls 3 at a specific angle) of the container 1. In the embodiment shown here, the measuring unit 10 is fixedly installed in the measurement carrier 22 in such a way that at least one radiation source 11 and at least one sensor 12 are located in a measurement region 17 on the base 5 of each container 1. In each container 1, the measurement region 17 is positioned in the edge region of the container 1 in which the greatest accumulation of liquid sample 2 is located when the container 1 is shaken.

In the embodiment shown here, the measuring unit 10 comprises a radiation source 11 and two sensors 12. The optical axis oA of the radiation source 11 and the optical axis oA of the sensor 12 are arranged at a defined angle 29 to one another. The angle is preferably 90°. The radiation source 11 and the two sensors 12 are arranged in a common holder (not depicted), which represents the measuring unit 10. This arrangement of the measuring unit 10 ensures that a liquid column that is as high as possible is present above at least one sensor 12 of the measuring unit 10, even in the case of small sample volumes. This is necessary for a reproducible measurement of the scattered light of the sample 2.

FIG. 2 shows the example of a plan view onto a container 1 of the matrix 1M for a sample 2. In this embodiment, the container 1 is defined by four walls 3 and a base, which produces the square cross-sectional shape. The advantage of the square cross-sectional shape is that the shaking movement of the matrix 1M of the containers 1 results in a uniform structure of the liquid column of the sample 2 in the area of the corners 7 of the containers 1. The measurement region 17 is consequently provided in the area of the one corner 7. Every container 1 can be designed in such a way that at least the measurement region 17 on the base 5 of the container 1 is permeable to the electromagnetic radiation in both directions orthogonal to the base 5. The measurement region 17 of each container 1 is configured in the edge region, in which the liquid column of the sample 2 forms during the shaking movement. One respective measuring unit 10 is permanently assigned to said measurement area 17, when the matrix 1M is mounted on the measurement carrier 22 (see FIG. 4.).

Even though FIG. 2 describes only the embodiment of the containers 1 with a square cross section, this is not construed as a limitation of the invention. Any type of angular container 1 can be used with the measurement carrier 22 and its measuring units 10. The containers 1 can thus take on a wide variety of implementations of the angular cross-sectional shape. The only requirement is that, when the plurality of containers 1 in the form of the matrix 1M and rigidly connected to one another is shaken, a liquid column suitable for the measurement by the measuring unit 10 forms in the measurement region 17 of each of the containers 1 filled with the sample.

Figure 3A:
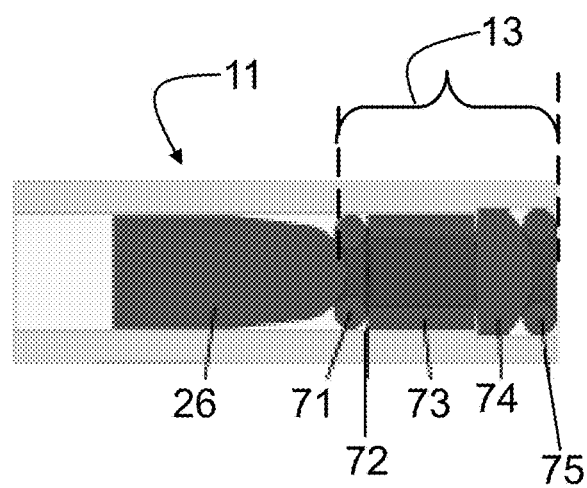
FIGS. 3A-3B respectively show a cross section through the optical system for collimating the electromagnetic radiation emitted by the radiation source.
Figure 3B:
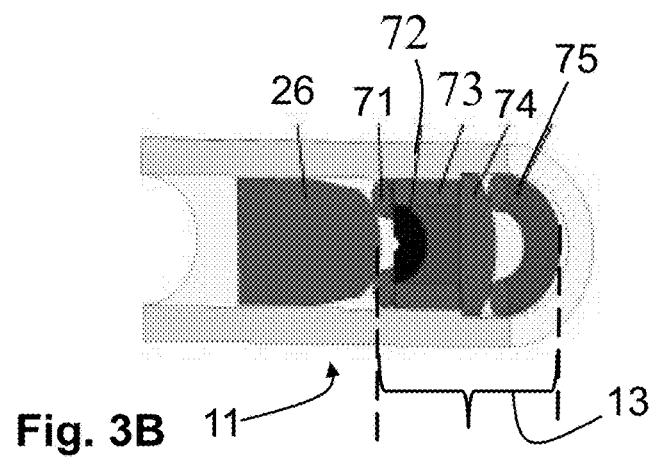

FIGS. 3A-3B respectively show a cross section through the optical system 13 for collimating the electromagnetic radiation emitted by the radiation source 11. In one embodiment, the radiation source 11 comprises the light-emitting diode 26, which is followed by an optical system 13. The optical system 13 comprises a spacer 71, a pinhole aperture 72, another spacer 73, an optical lens 74 and a spacer 75. The pinhole aperture 72 is used to reduce the specific radiation angle of the light-emitting diode 26. The light cone emanating from the pinhole aperture 72 is focused by the optical lens 74, as a result of which a high depth of focus of the projection is achieved.

Figure 4:
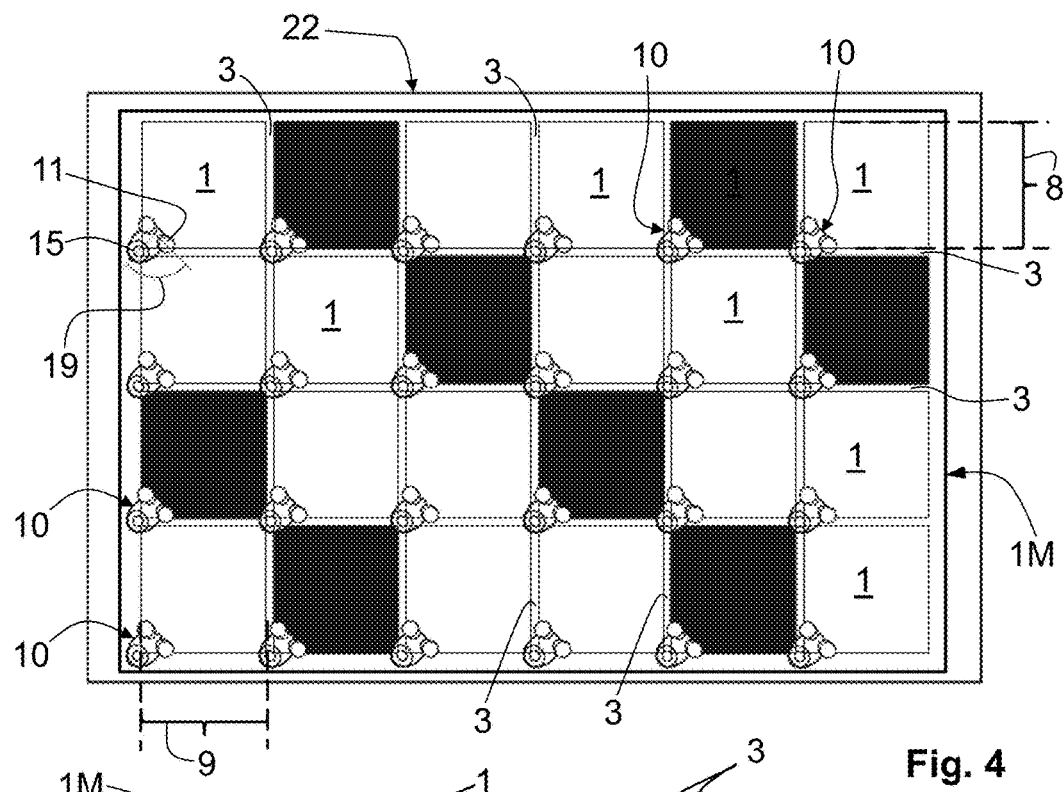
FIG. 4 shows a plan view onto an arrangement of a matrix of a plurality of containers on a measurement carrier.

FIG. 4 shows a plan view onto a possible embodiment of an arrangement of a matrix 1M of a plurality of containers 1 on a measurement carrier 22. As shown in FIG. 4, the plurality of containers 1 of the matrix 1E are rigidly connected to one another and separated from one another by the walls 3. In the embodiment of the matrix 1E shown here, the containers 1 are regularly arranged in columns 9 and rows 8. The measuring units 10 are arranged or integrated on the measurement carrier 22. By positioning the matrix on the measurement carrier 22, one respective measuring unit 10 is fixedly assigned to one respective container 1 of the matrix. The containers 1 of the matrix 1M and the measuring units 10 associated with the containers 1 are mechanically immovable relative to one another. In the embodiment shown here, all the containers 1 have a square cross section. According to the embodiment shown here, the matrix 1M on the measurement carrier 22 has twenty-four containers 1. With regard to the size and number of the containers 1 in the matrix 1M, other arrangements are conceivable for a person skilled in the art.

Figure 5A:
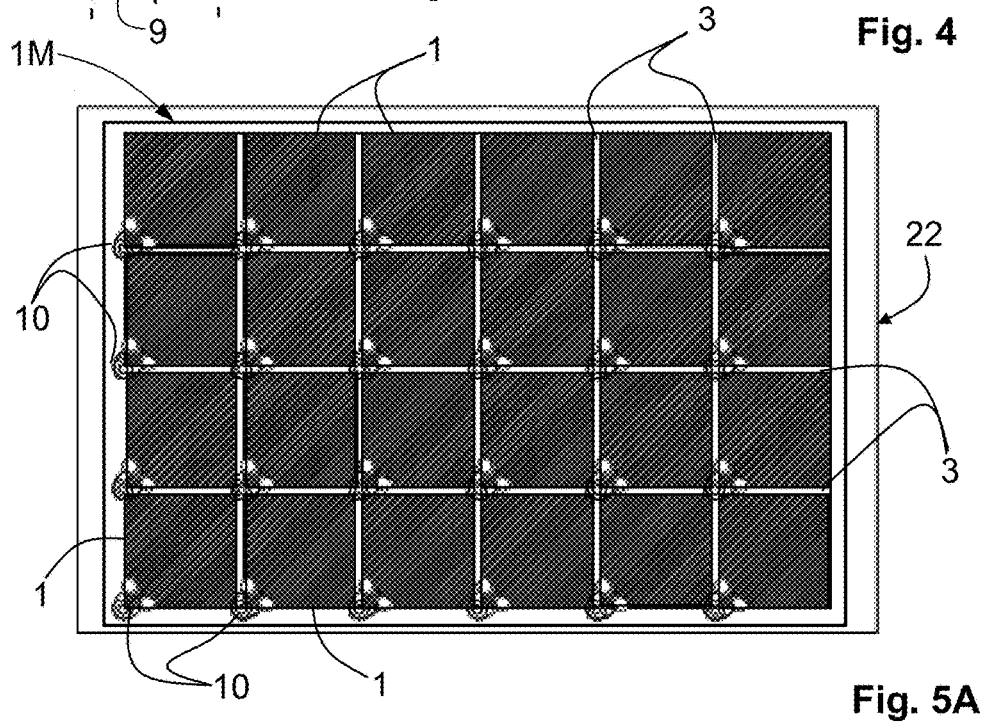
FIG. 5A shows a plan view onto an arrangement of a matrix of a plurality of containers which are in rigid connection with the measurement carrier.

FIG. 5A shows a plan view onto a further embodiment of the matrix 1M of a plurality of containers 1. Using the measuring units 10 of the measurement carrier 22, the measurements in all the containers 1 of the matrix 1M can be carried out essentially simultaneously. This measuring technique can be implemented when the walls 3 of the respective containers 1 (wells) are not transparent to the wavelength of the electromagnetic radiation of the radiation source 11 and to the scattered light produced thereby on the sample 2. The walls 3 are very simply made of a non-transparent plastic.

Figure 5B:
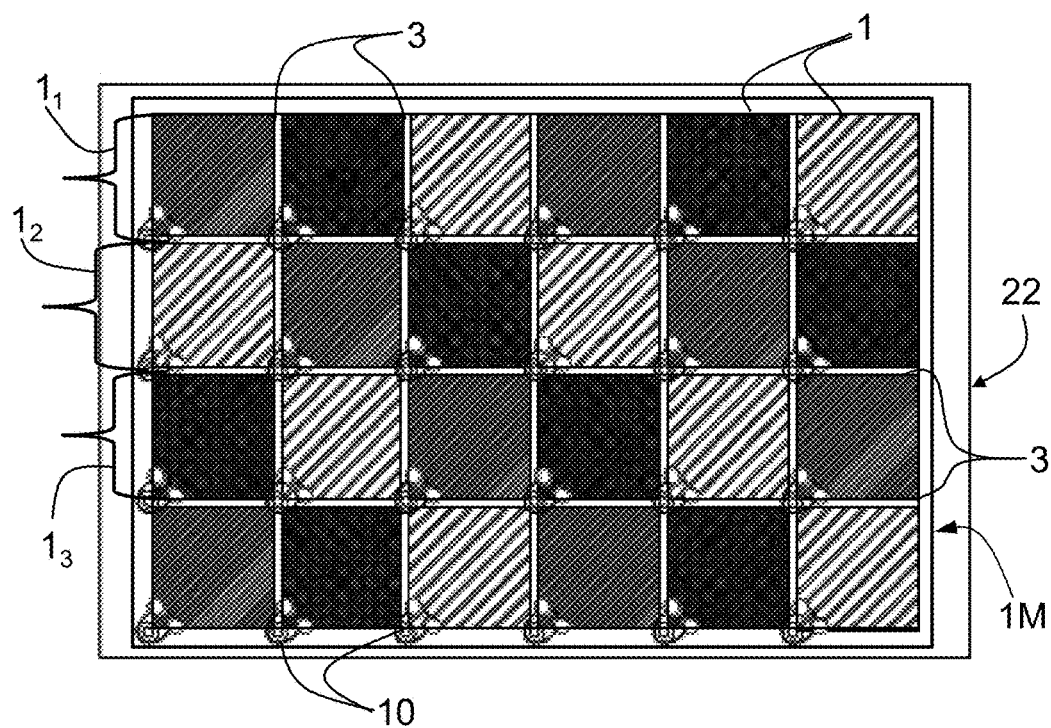
FIG. 5B shows a plan view of an arrangement of the matrix of a plurality of containers on the measurement carrier, wherein the containers are divided into groups.

FIG. 5B shows a plan view onto the matrix 1M of a plurality of containers 1 in rigid connection with one another, wherein, in one possible embodiment, the containers 1 are arranged in groups $1_1$, $1_2$ and $1_3$ and the measurement in the groups $1_1$, $1_2$ and $1_3$ is conducted at different times. The number of groups $1_1$, $1_2$ and $1_3$ is not stated as a limitation of the invention. All the containers belonging to one group ($1_1$, $1_2$ or $1_3$) are identified by the same hatching. Within the defined group $1_1$, $1_2$ or $1_3$ then, the measurement in the containers 1 is conducted simultaneously, while the successive measurement of different groups takes place with a time delay of less than 2 seconds. This measuring technique is used when, in a matrix arrangement of the containers 1, the walls 3 of said containers are transparent. A transmission of light from one measuring unit 10 to sensors 12 of other measuring units 10 is thereby prevented. The arrangement of the groups $1_1$, $1_2$ and $1_3$ primarily prevents diagonal extraneous coupling.

Figure 5C:
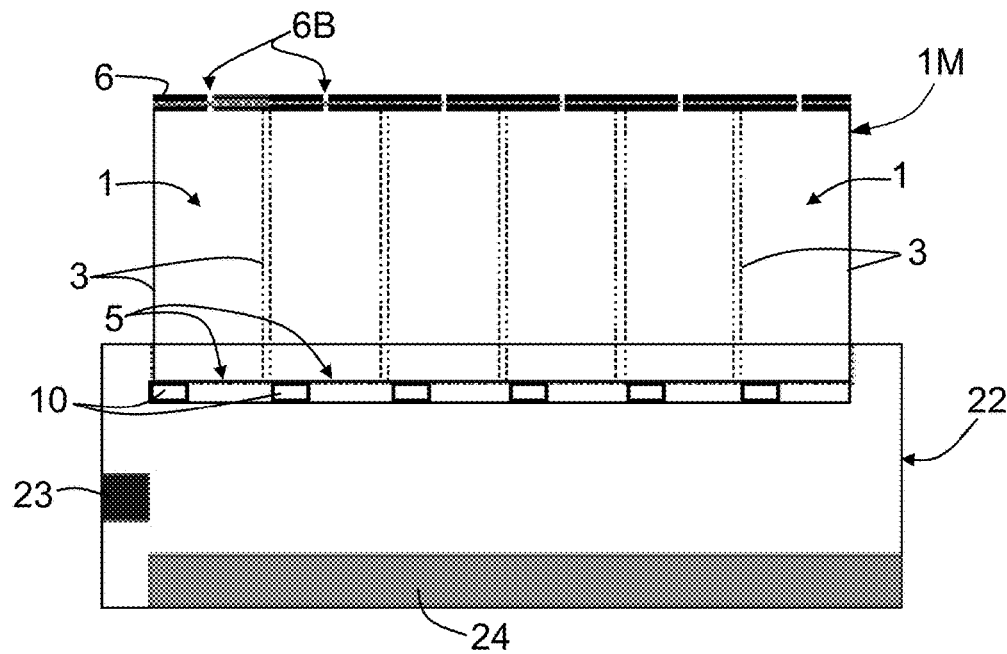
FIG. 5C shows a side view of the arrangement of the matrix of a plurality of containers which is rigidly connected to an embodiment of the measurement carrier.

FIG. 5C shows a side view of the matrix 1M of the plurality of rigidly connected containers 1 on an embodiment of the measurement carrier 22. The measurement carrier 22 serves to accommodate the matrix 1M of the containers 1 (microbioreactors). In this embodiment, all the containers 1 are covered during the measurement process. The cover 6 is provided with bores 6B. Each container 1 is associated with one bore 6B. The cover 6 is a sterile barrier in the form of a membrane or some other porous, semipermeable layer. The sterile barrier allows the exchange of gas in both directions, by means of which microorganisms are supplied with oxygen, for example, or metabolic products such as $CO_2$ are removed. The measurement carrier 22 holds the plurality of measuring units 10 at defined positions, which, when the matrix 1M is mounted on the measurement carrier 22, are respectively permanently assigned to the base 5 of every container 1. The measurement carrier 22 further includes an electronics module 24, which is communicatively connected to the measuring units 10. The supply of power to the measuring units 10, the electronics module 24 and the data connection 23 takes place in a manner known in the prior art.

Figure 6A:
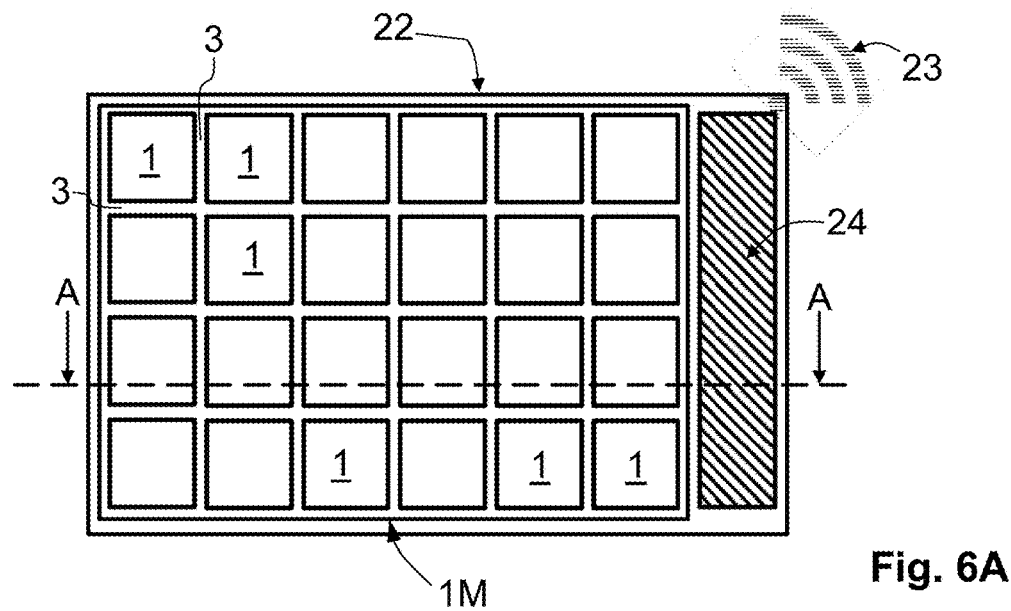
FIG. 6A shows a plan view onto an arrangement of the matrix of a plurality of containers 1 in rigid connection with one another on a different embodiment of the measurement carrier.

FIG. 6A shows a plan view of a further embodiment of the matrix 1M of a plurality of containers 1, wherein the matrix 1M is positioned on the measurement carrier 22. An electronics module 24 is additionally configured on the measurement carrier 22, which provides for the supply of electricity to the measuring units 10 and communication to measuring units 10 (within a sensor network) on the measurement carrier 22 via conventionally known connection technologies. A data connection 23 to a base station 30, i.e. computer (see FIG. 9) is provided. In the embodiment described here, the data connection 23 is a wireless communication. Using the communication with the base station 30, i.e. computer (for data processing/data recording), the active containers 1 filled with a sample 2 and at least one measurement carrier of the measurement system can be consolidated to one communicating network of measuring units 10.

Figure 6B:
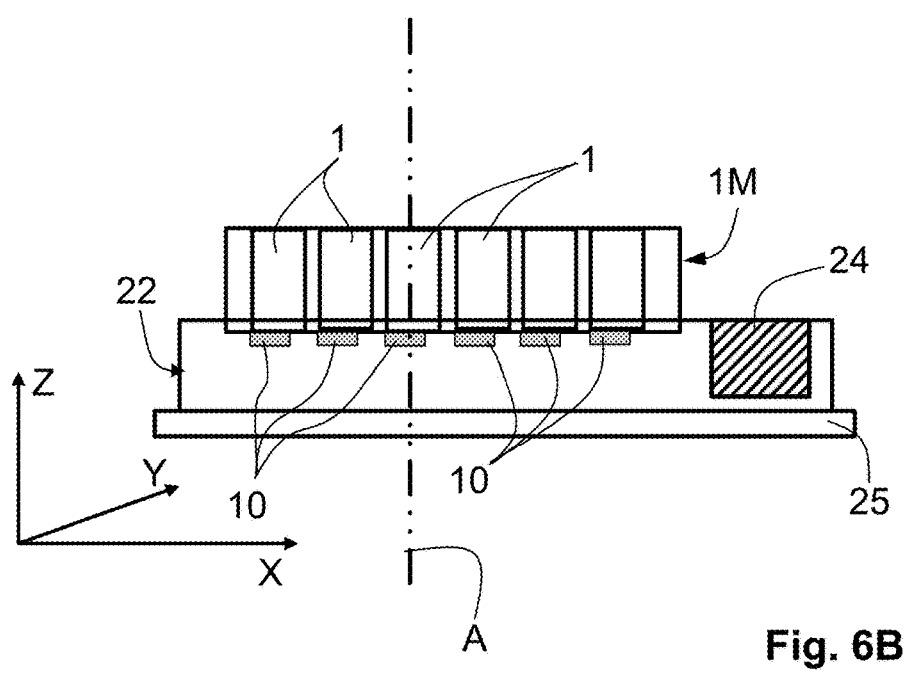
FIG. 6B shows a sectional view along the section line of the measurement carrier for the matrix of containers identified in FIG. 6A, wherein the measurement carrier is positioned on a movement device.

FIG. 6B shows a sectional view along the section line A-A through the measurement carrier 22 and the mounted matrix 1M identified in FIG. 6A. The measurement carrier 22 is positioned on the one movement device 25, so that a defined movement can be imposed on the matrix 1M of the containers 1 fixedly connected to the measurement carrier 22. To measure the sample 2 in the individual containers 1 and to determine at least one variable of the sample 2, an uninterrupted, defined, radial movement of the matrix 1M of the containers 1 about a fixed axis A, orthogonal to the gravitational force, can be carried out from the measurement carrier 22. The movement is at least composed of movement components in X-coordinate direction X and/or Y-coordinate direction Y. On the measurement carrier 22, the measuring units 10 of the measurement carrier 22 are fixedly assigned to the matrix 1M of the individual containers 1 for the determination of at least one variable of the sample 2. The measured values of the measuring units 10 are transmitted to the base station 30 by means of the electronics module 24 or the data connection 23 (see FIG. 9).

Figure 7A:
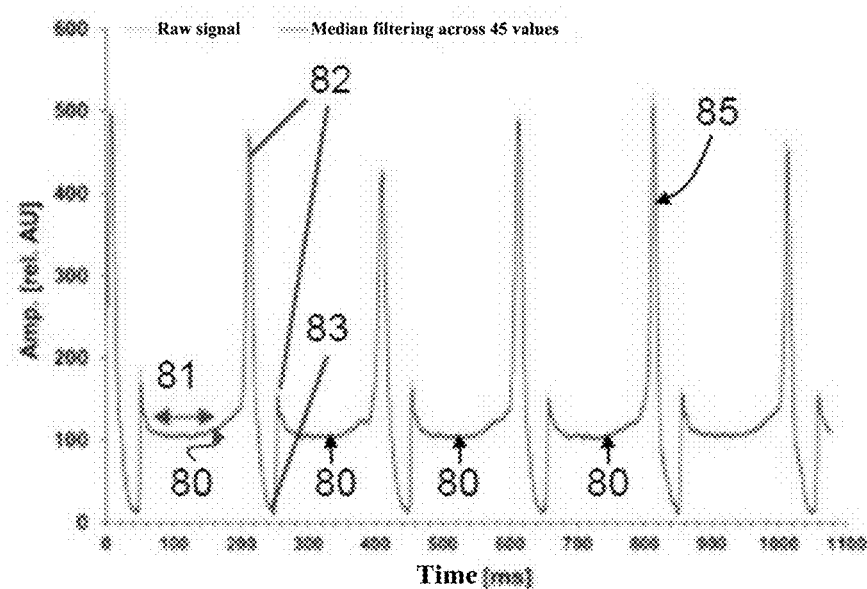
FIG. 7A shows a graphic representation of a typical scattered light signal for a cell suspension of constant optical density over a defined time interval, which is characterized by periodically recurring blocks.

FIG. 7A shows a graphic representation of a typical scattered light signal for a cell suspension of constant optical density, which is characterized by periodically recurring blocks. As a result of the movement of the containers 1 (microbioreactors) about a fixed axis A, unequal distributions of the liquid sample 2 occur in the containers 1 (see FIGS. 1A to 1C). The liquid sample 2 is displaced in the direction of the walls 3 of each container of the matrix 1M by centripetal forces. Assuming high movement frequencies and small sample volumes, fluid distributions can arise, in which larger areas of the base 5 of the container 1 are not covered by liquid and are therefore not suitable for the measurement. Using the continuous measurement of the scattered light at a high measuring frequency of at least 10 kHz, the periodically changing liquid volume of the sample 2 over the measuring unit 10 can be temporally resolved over a defined time period. The typical signal of a cell suspension of constant optical density is characterized by periodically recurring blocks (similar to a square-wave modulation) with areas 80 of low signal deviation over a definable time interval 81, signal peaks 82 in the edge region of the blocks and gaps 83 of low scattered light amplitude. The relevant measurement areas are those created during the movement when the liquid sample 2 passes over the measuring unit 10. In the time interval with the largest liquid volume element above the measuring unit 10, the distance of the water/air interface is statistically the greatest, as a result of which boundary surface reflections strike the measuring unit 10 statistically less frequently, i.e. are attenuated by the optical path within the sample 2, and contribute less to the interference of the scattered light signal. Other interference in the form of continuous measurement noise can be caused by air bubbles, foam and the inhomogeneity of the sample during the movement of the sample 2. Median filters or Savitzky-Golay filters with a defined window width are used to filter the raw signal, i.e. reduce the measurement noise. After prefiltering, relevant measurement areas are selected and extracted using the criteria specified below or a combination of a number of criteria. A small standard deviation of the scattered light signal 85 within a defined time interval ("plateaus"; region 80) is thus obtained. This also results in a low signal-to-noise ratio relative to the height of the scattered light signal (see FIG. 7D) in the areas 80.

Figure 7B:
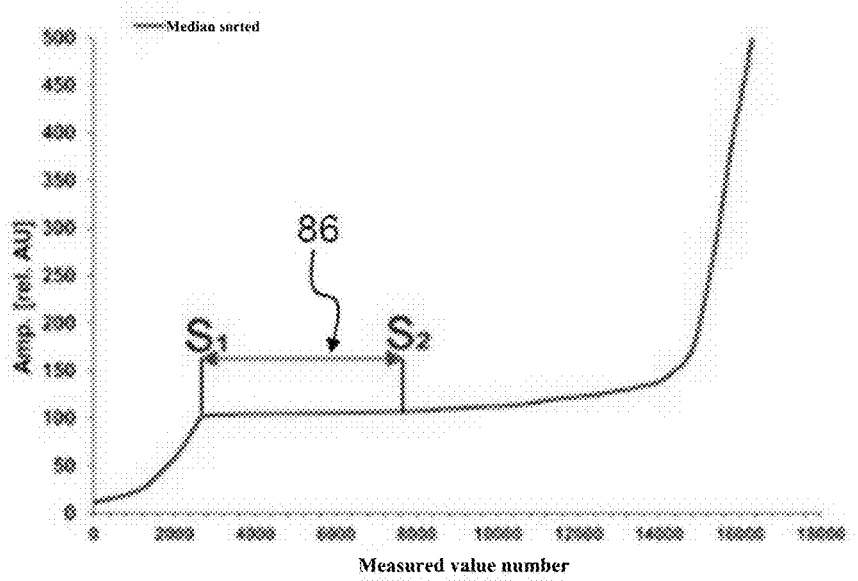
FIG. 7B shows a graphic representation of the size sorting of scattered light signal data from a defined time interval of FIG. 7A.

FIG. 7B shows a graphic representation of the sorting of accumulated measured values of the same scattered light amplitude. In this step, existing measurement noise in the raw signal is reduced by one of the above-specified filter methods. The filtered measurement data of the scattered light amplitude is then accordingly sorted from small to large values. By sorting the accumulated measured values of the same scattered light amplitude, a contiguous interval 86 is formed between S1-S2. S1 and S2 are parameters of the method and can be specified before and during the physical recording of the scattered light, or determined in an automated manner by derivation (see FIG. 7C) of the sorted scattered light signal profile.

Figure 7C:
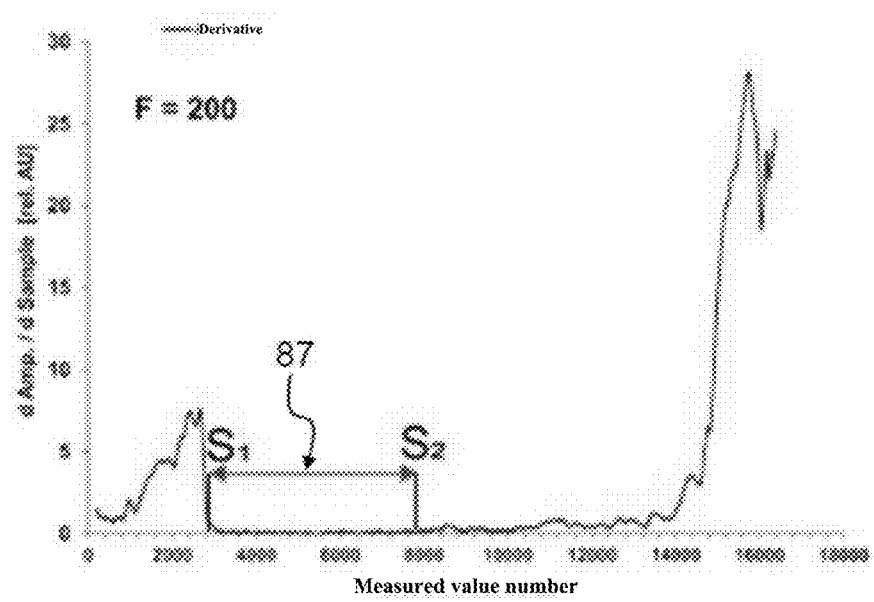
FIG. 7C shows a graphic representation of the derivative of the sorted scattered light signal profile of FIG. 7B.

FIG. 7C shows a graphic representation of the derivative of the sorted scattered light signal profile of FIG. 7B. The derivation allows the specification of a threshold (threshold value) for the maximum slope of the sorted scattered light signal profile (curve profile). A contiguous interval 87 with the lowest slope is thus determined. The arithmetic mean of all the measurement data within the interval is subsequently calculated, thereby creating a new measured value for conversion into at least one of the reference parameters OD600, biomass concentration and cell concentration.

Figure 7D:
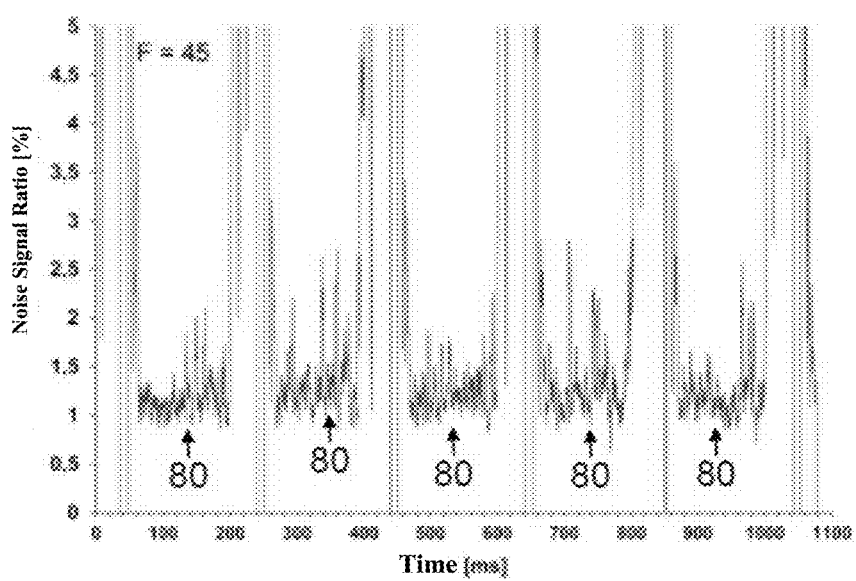
FIG. 7D shows a graphic representation of the measurement noise of FIG. 7A.

FIG. 7D shows a graphic representation of the measurement noise. Parallel to the physical recording of the scattered light, the existing measurement noise in the raw signal is reduced by one of the filter methods specified above.

Figure 8:
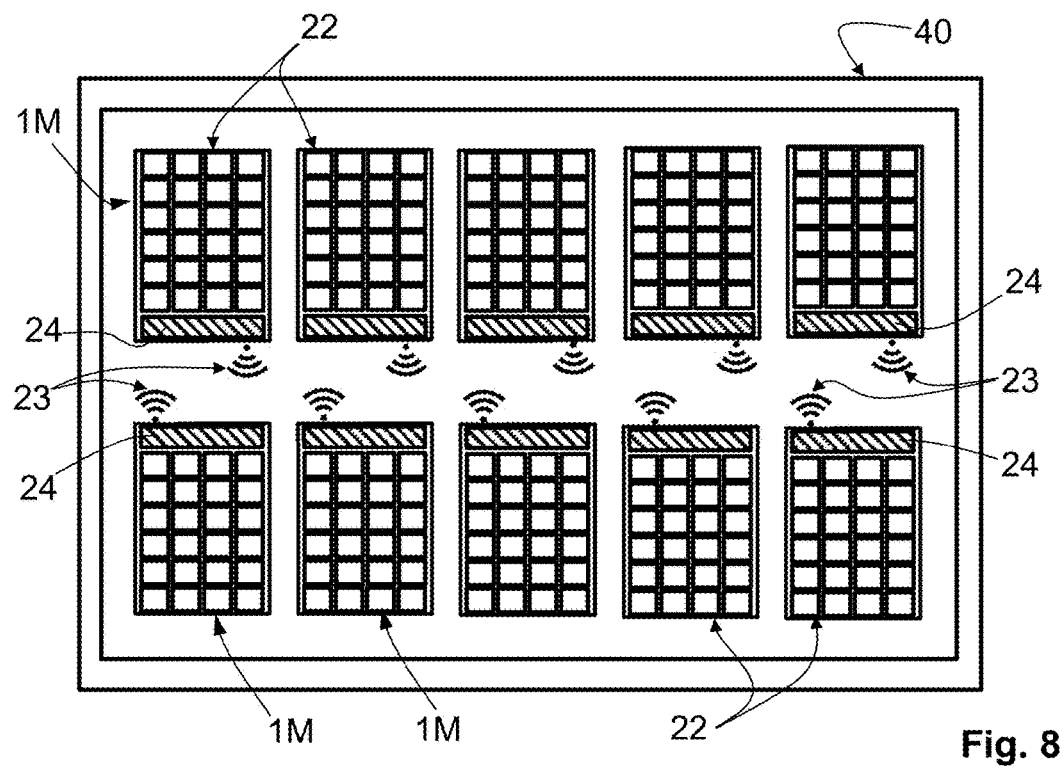
FIG. 8 shows the arrangement of several microtiter plates with the square containers in an incubator.

FIG. 8 shows the arrangement of a plurality of measurement carriers 22 in an incubator 40, each of said measurement carriers having one respective matrix 1M of a plurality of containers 1 arranged upon it. In the measurement system shown here, ten measurement carriers 22 (measuring units) with a matrix 1M of twenty-four respective containers 1 for the samples 2 arranged upon it, have been brought into the incubator 40. The continuous, optical measurement and recording of scattered light occurring at the biological material in the individual containers 1 as a result of the irradiation with light can thus be achieved. Using a single measurement carrier 22, an interruption-free, non-invasive and simultaneous measurement can be carried out on the twenty-four containers 1 per measurement carrier 22 during use in incubators 40 in a radial shaking operation for bacterial and mammalian cell cultures. By miniaturizing the measurement carriers 22, up to ten measurement carriers 22 can be arranged and studied at the same time within one shaker/incubation environment. The communication of the individual measuring units 10 associated with the containers 1 of the respective carrier 22 (measuring unit) is controlled by the electronics module 24. The communication of the measuring units 10 takes place via a respective data connection 23, such as a radio link (Bluetooth, WLAN).

Figure 9:
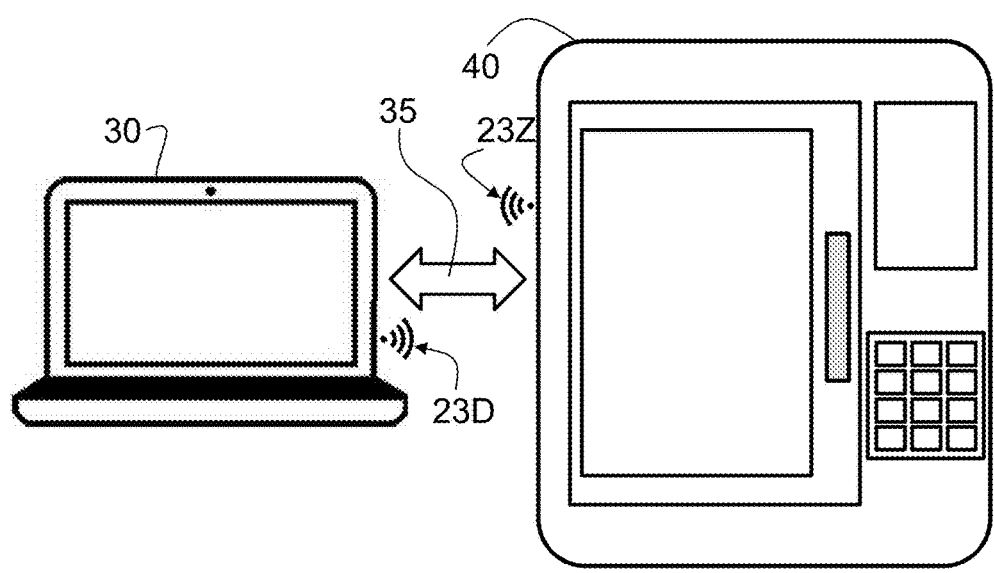
FIG. 9 shows a schematic arrangement of an incubator to a computer, which takes care of the recording and analysis of the measurement results of the substances in the containers of the microtiter plates that are placed in the incubator.

FIG. 9 shows a schematic arrangement of an incubator 40 in connection with a base station or computer 30, which takes care of the recording and analysis of the measurement results of the substances in the containers 1 (microbioreactors). In order to support the processes of interest in a particular study, the measurement carriers 22 with the plurality of containers 1 can be moved within the incubator 40. This is preferably done mechanically. The appropriate, generally known devices are, for example, agitators, shakers or rockers. These devices are commercially available in a variety of embodiments that are able to move a container 1, or even a plurality of containers 1 on a measurement carrier 22 simultaneously in a defined manner. All of these devices can be accommodated in the incubator 40. In order to receive data from the measurement carriers 22 in the incubator 40 and to send control data, for example, from the base station 30 to the incubator 40 itself or to the electronics modules 24 of the carriers 22, the base station 30 is connected to the incubator 40 via a bidirectional communication connection 35.

According to one preferred embodiment, each measuring unit 10 has a data connection 23, a radio transmitter/receiver, by means of which a local radio network to a permanent central data connection 23Z, likewise a radio transmitter/receiver, is established. Bluetooth or WLAN, for example, can be used for the data transfer technology being employed. In addition, all the measuring units 10 have a device-internal permanent data memory for recording measurement data. The central radio transmitter/receiver is connected to a base station 30 (device for data processing/data recording), such as a computer, e.g. a desktop computer, a notebook computer, a tablet computer or a smart phone, via a data interface 23D.

Figure 10:
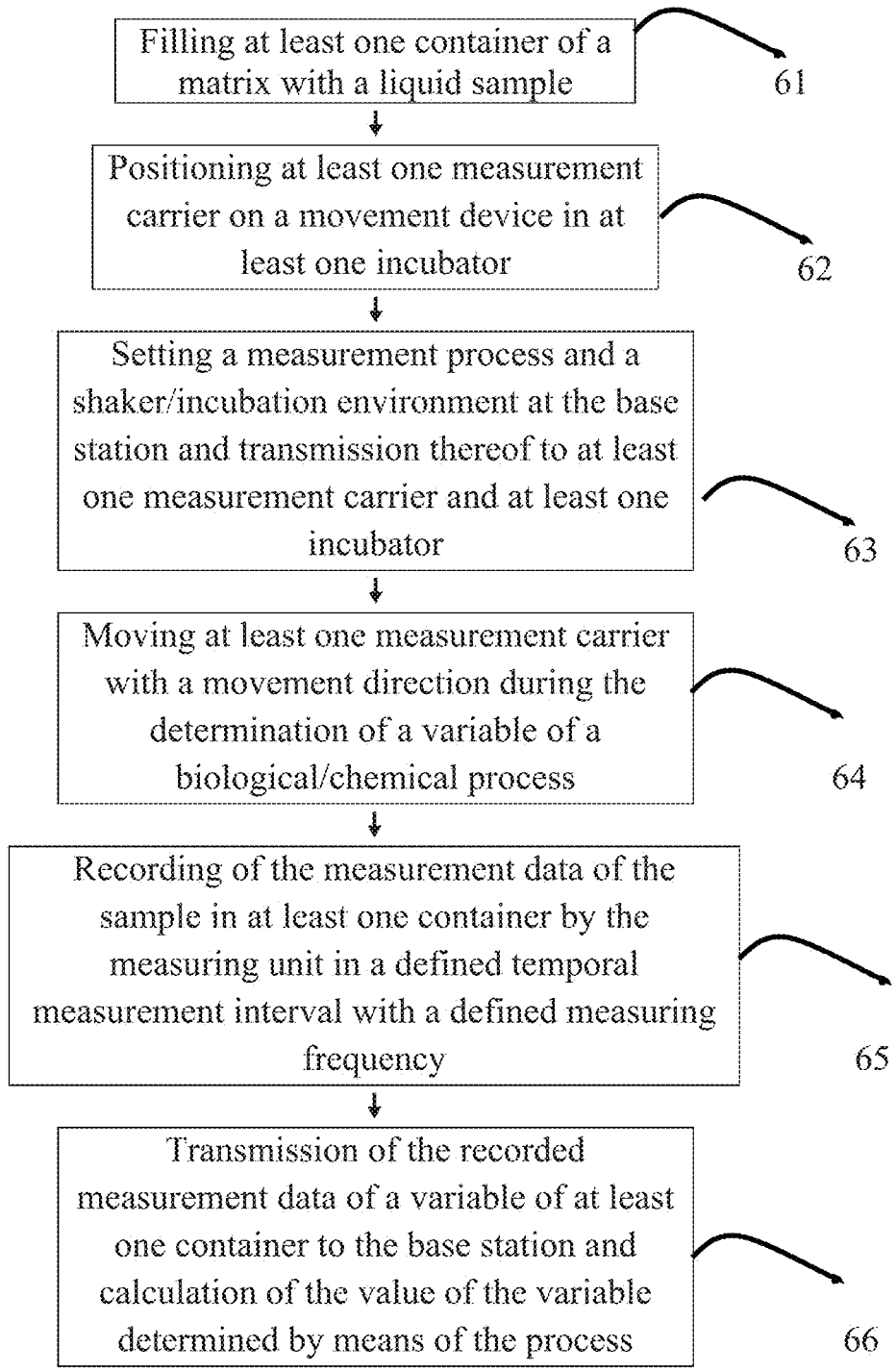
FIG. 10 shows a flow chart of an embodiment of the method according to the invention.

FIG. 10 shows a flow chart of the method according to the invention for the parallelized recording of cell and biomass concentrations of cell cultures (liquid sample 2). In a step 61 at the beginning of the method according to the invention, at least one container 1 of a carrier 22 is filled with a liquid sample 2 (the consistency and property of the sample is described sufficiently above). The containers 1 are fixedly arranged on the carrier in columns 9 and rows 8 (in the form of a matrix). The opening 4 of the containers 1 can be closed by a cover 6, so that the liquid sample 2 does not escape from the container 1 during the measuring process.

In a next step 62, at least one measurement carrier 22 is attached to a movement device 25 in at least one incubator

40, which is communicatively connected to the base station 30. It should be noted that, in another embodiment of the method, it is also possible to not have the incubator.

In step 63, a measurement process and a shaker/incubation environment are set at the base station 30. The settings are transmitted to at least one measurement carrier 22 and, if appropriate, to at least one incubator 40 (if necessary also to the movement device 25). Without being restricted thereto, possible settings of the measurement process are, for example, the incubation conditions, the radial movement pattern (such as repetition frequency and direction of rotation—since the movement type "radial" was previously specified), the movement device 25, the control of the radiation source 11, the definition of the measuring frequency for a temporal measurement interval (to generate a measured value, the user has to specify only that a measured value is to be recorded every 10 seconds, for example) or the setting of the wavelength emitted by the radiation source 11.

In step 64, the movement of at least one carrier 22 by means of its associated movement device 25 is carried out. The determination of a variable of the biological/chemical process is performed during the movement of the carrier 22 according to a defined movement pattern. The movement of the carrier 22 can be carried out, for example, without interruption and with a defined, radial movement about a fixed axis, orthogonal to the gravitational force S.

In a step 65, which is temporally parallel to step 64, the measuring unit 10 is used to record the measurement data of the liquid and moved sample 2 in at least one container 1. The recording of the measurement data takes place within a defined temporal measurement interval with a defined measuring frequency of at least 10 kHz. In each container 1, in which there is a sample, the measurement data is recorded with the sensor of the measuring unit 10. One measuring unit 10 is permanently assigned to each of the respective containers 1, wherein the measuring units 10 are fixedly arranged on the measurement carrier 22 for the containers 1 (e.g. microtiter plate). The measuring unit 10 comprises the controllable radiation source 11 and at least one sensor 12.

Finally, in step 66, the recorded measurement data of a variable in at least one container 1 is transmitted. The measurement data is transmitted from the incubator 40 to the base station 30 (or a suitable analysis unit). The value of the variable determined via the analysis process is calculated by means of the base station 30. The variable is, for example, the turbidity and the optical density of liquid samples, as well as in particular the cell density, biomass and cell concentration, pH, $O_2$ saturation of the liquid and the ambient temperature. To determine the pH or the $O_2$ saturation of the liquid, sensor pads (not depicted here) are glued into the container. The pH or the $O_2$ saturation are recorded as an optical response by the sensor 12 associated with the respective container that was previously illuminated by a light source. The relative saturation of dissolved oxygen in the respective sample 2 is regulated by changing the energy input during the movement of the containers 11 or the carrier 22 via the movement pattern of the movement device 10. It is particularly advantageous if the recorded measurement data is transmitted from the incubator 40 to the base station 30 by means of a radio link 23, because this eliminates a cable break as a source of a failure.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

LIST OF REFERENCE SIGNS

1 Container
$1_1, 1_2, 1^3$ Group
1M Matrix
2 Sample
3 Wall
3T Section
4 Opening
5 Base
5F Bottom surface
6 Cover
6B Bore
7 Corner
8 Line
9 Column
10 Measuring unit
11 Radiation source
11S Beam
12 Sensor
13 Optical system
14 Angle
15 Optical fiber
16 Optical filter
17 Measurement region
18 Cross section
19 Angle
20 Light
22 Measurement carrier
23 Data connection
23D Data interface
23Z Central data connection
24 Electronics module
25 Movement device
26 Light-emitting diode
27 Light cylinder
29 Angle
30 Base station
35 Bidirectional communication connection
40 Incubator
50 Signal pattern
51 Time derivative
61 Step
62 Step
63 Step
64 Step
65 Step
66 Step
71 Spacer
72 Pinhole aperture
73 Spacer
74 Optical lens
75 Spacer
80 Range
81 Time interval
82 Signal peak
83 Gap
85 Scattered light signal
86 Interval
87 Interval
A Axis
A-A Section line O Orthogonal
oA Optical axis
R Orthogonal direction
S Gravitational force
$S_1$ Parameter
$S_2$ Parameter
X X-coordinate direction
Y Y-coordinate direction
Z Z-coordinate direction

What is claim is:

1. A method for recording at least one variable in a plurality of containers for liquid samples during a biological/chemical process, wherein the method comprises the following steps:
   filling at least one container of a matrix comprising a plurality of containers, each of which has a square cross-sectional shape, with the liquid sample;
   placing the matrix onto a measurement carrier, wherein the one respective measuring unit of the plurality of measuring units in the measurement carrier, which includes at least one controllable radiation source for electromagnetic radiation and at least one sensor for detecting electromagnetic radiation, is permanently assigned to a base of each container of the matrix;
   moving the measurement carrier in a X-coordinate direction and in a Y-coordinate direction and thereby recording at least one variable during the biological/chemical process in at least one container of the matrix;
   wherein the movement of the measurement carrier is carried out without interruption and with a defined radial movement about a fixed axis orthogonal to the gravitational force, and
   wherein, as a result of the movement, a measurement area is formed in the region of a corner in each container of the matrix and, for each filled container, at least one controllable radiation source radiates electromagnetic radiation through the base into the measurement region and at least one sensor detects electromagnetic radiation from the measurement region through the base.

2. The method according to claim 1, wherein a beam originating from the radiation source is radiated at an angle through the base into the respective container of the matrix, and wherein an optical fiber of the optical sensor is arranged at an angle to an orthogonal of the base and receives electromagnetic radiation from the liquid sample through the base.

3. The method according to claim 1, wherein a beam originating from the radiation source is radiated at an angle through the base into the respective container of the matrix, and wherein the optical sensor is arranged at an angle to an orthogonal of the base and receives electromagnetic radiation from the liquid sample through the base.

4. The method according to claim 1, wherein the containers of the matrix are measured by means of the measuring units of the measurement carrier assigned to said containers in such a way that the containers are grouped, and the respective measured values from the grouped containers are obtained in a time-offset manner.

5. The method according to claim 1, wherein at least one variable in each container of the matrix is recorded in a defined temporal measurement interval with a measuring frequency of at least 10000 measurement events per second, and wherein the recorded measurement data of at least one variable of each container of the matrix is processed individually according to a mathematical method in a defined temporal measurement interval and converted to a value of the variable which is determined after the beginning of the process.

6. The method according to claim 5, wherein the recorded measurement data is transmitted to a base station by means of a data connection.

* * * * *